United States Patent
Sedun et al.

(10) Patent No.: US 6,486,097 B2
(45) Date of Patent: Nov. 26, 2002

(54) HERBICIDAL FATTY ACID AND MALEIC HYDRAZIDE SALT COMPOSITIONS

(75) Inventors: Frederick S. Sedun, Victoria (CA); Cameron D. Wilson, Victoria (CA)

(73) Assignee: W. Neudorff GmbH KG (DE)

( * ) Notice: Subject to any disclaimer, the term of this patent is extended or adjusted under 35 U.S.C. 154(b) by 0 days.

(21) Appl. No.: 10/050,622

(22) Filed: Jan. 16, 2002

(65) Prior Publication Data

US 2002/0103085 A1 Aug. 1, 2002

Related U.S. Application Data

(63) Continuation of application No. 09/480,503, filed on Jan. 10, 2000, now Pat. No. 6,383,985.

(51) Int. Cl.$^7$ .............................................. A01N 43/58
(52) U.S. Cl. ...................................................... 504/137
(58) Field of Search ........................................ 504/137

(56) References Cited

U.S. PATENT DOCUMENTS

| | | | | |
|---|---|---|---|---|
| 2,626,862 A | * | 6/1953 | Zimmerman et al. | 71/2.7 |
| 4,265,654 A | | 5/1981 | Takematsu et al. | 71/86 |
| 4,309,208 A | | 1/1982 | Takematsu et al. | 71/86 |
| 4,556,410 A | | 12/1985 | Ronning et al. | 71/78 |
| 4,975,110 A | | 12/1990 | Puritch et al. | 71/113 |
| 5,035,741 A | * | 7/1991 | Puritch et al. | 71/113 |
| 5,098,467 A | | 3/1992 | Puritch et al. | 71/113 |
| 5,098,468 A | | 3/1992 | Puritch et al. | 71/113 |
| 5,106,410 A | | 4/1992 | Puritch et al. | 71/113 |
| 5,196,044 A | | 3/1993 | Caulder et al. | 504/127 |
| 5,541,153 A | | 7/1996 | Coultas | 504/185 |
| 5,683,959 A | | 11/1997 | Caulder et al. | 504/127 |
| 5,683,961 A | | 11/1997 | Caulder et al. | 504/130 |
| 5,683,962 A | | 11/1997 | Caulder et al. | 504/137 |
| 5,703,011 A | | 12/1997 | Caulder et al. | 504/130 |
| 5,703,012 A | | 12/1997 | Caulder et al. | 504/130 |
| 5,703,013 A | | 12/1997 | Caulder et al. | 504/131 |
| 5,703,014 A | | 12/1997 | Caulder et al. | 504/142 |
| 5,703,019 A | * | 12/1997 | Evans et al. | 504/320 |
| 5,714,435 A | | 2/1998 | Coultas | 504/137 |
| 5,919,734 A | | 7/1999 | Jones | 504/320 |

FOREIGN PATENT DOCUMENTS

| | | | |
|---|---|---|---|
| BE | 861231 | | 12/1997 |
| DE | 2748646 | | 5/1979 |
| DE | 2906570 | | 8/1980 |
| EP | 134339 | * | 3/1985 |
| FR | 2330319 | | 7/1977 |
| GB | 2067405 | | 1/1980 |
| JP | 73001497 | * | 8/1964 |
| JP | 73008804 | * | 2/1970 |
| JP | 51073130 | | 6/1976 |
| JP | 52076433 | | 6/1977 |
| JP | 11335209 | * | 1/1999 |
| RO | 80369 | * | 12/1982 |
| RU | 2030151 | | 3/1995 |
| WO | 8903178 | * | 4/1989 |
| WO | 9400985 | | 1/1994 |

OTHER PUBLICATIONS

Gichner et al, Differential response to three alkylating nitrosocompounds and three agricultural chemicals in the Salmonella and in the Tradescantia, Arabidopsis and barley mutagenicity assays, Biol. Zentralbl, 101(3), 375–83, 1982.*

Chopra, et al., "Effect of Some Auxins and Antiauxins on Protonemal Growth and Bud Formation in *Bryum pallescens* Schleich. Ex Schwaegr. Grown In Vitro," *Plant Science*, vol. 51: 251–256 (1987).

Chukwuma, J., et al., "Effect of Seed–Pretreatment with Some Growth Regulators on Germination, Growth and Yield of Cowpea (*Vigna sinensis* Endl.)," *Japan Jour. Crop Sci.*, vol. 58., No. 4: 641–647 (1989).

Nicoloff, H., et al., "Caffeine Prevents the Maleic Hydrazide–Triggered "Adaptive Response" in *Hordeum vulgare* and *Vicia faba*," *Biol. Zent.bl.*, vol. 111: 114–119 (1992).

Parr, T. W., et al., "Comparison of root– and shoot–acting growth retardants on a grass clover sward," *Weed Research*, vol. 27: 69–78 (1987).

Sarma, C.M., et al., "Interactions between Gibberellic Acid and Maleic Hydrazide on the Elongation Growth of Cucumber Hypocotyls in vivo," *Proc. Nat. Acad. Sci. India*, vol. 56 (B), II: 179–182 (1987).

White, L., "Growth Regulators' Effect on Crested Wheatgrass Forage Yield and Quality," *J. Range Management*, vol. 42, No. 1:46–50 (Jan. 1989).

* cited by examiner

*Primary Examiner*—Alton Pryor
(74) *Attorney, Agent, or Firm*—Nutter McClennen & Fish LLP

(57) ABSTRACT

Compositions and methods for treating undesired weeds are disclosed. The compositions include a carboxylic acid components and maleic hydrazide derivatives, preferably as an ammonium salt.

17 Claims, No Drawings

HERBICIDAL FATTY ACID AND MALEIC HYDRAZIDE SALT COMPOSITIONS

CROSS REFERENCE TO RELATED APPLICATIONS

This application is a continuation of U.S. patent application Ser. No. 09/480,503, filed on Jan. 10, 2000, now U.S. Pat. No. 6,383,985 entitled "Herbicidal Fatty Acid and Maleic Hydrazide Salt Compositions," which is expressly incorporated herein by reference.

BACKGROUND OF THE INVENTION

Control of undesired vegetation, e.g., weeds, is extremely important in achieving high crop efficiency and for aesthetic appearances at commercial and residential areas. Selective control of the growth of weeds, especially in crops as rice, soybean, sugar beet, corn (maize), potato, wheat, barley, tomato and plantation crops is very desirable. Unchecked weed growth in such crops can cause significant reduction in productivity and thereby result in increased costs to the consumer. The control of undesired vegetation in noncrop areas, e.g., residential areas, is also important.

One approach to control undesired vegetation is by defoliation. Defoliation can be accomplished by leaf injury with certain herbicides. The herbicide can be either of the contact or systemic variety. A contact herbicide requires that a substantial portion of the plant be contacted with the active ingredient of the herbicide being applied. A systemic herbicide translocates through the plant.

Certain herbicides include fatty acids as a component of the active ingredient. Fatty acid herbicides are known in the art and are generally considered to be environmentally friendly. Fatty acid herbicides are typically supplied as concentrates that are diluted with water and applied as an oil-in-water emulsion. These concentrates usually contain the fatty acid active ingredient an emulsifying agent including surfactants, or oils. Application rates vary but usually the fatty acid emulsions are applied at application rates of at least 50–100 gallons or more per acre and deliver the active fatty acid herbicide at concentrations of 1–8% by weight.

For example, U.S. Pat. Nos. 4,975,110; 5,106,410 and 5,098,467 disclose fatty acid herbicidal compositions that contain C8–12 fatty acids, a surfactant and water with pelargonic acid being a preferred fatty acid herbicide. U.S. Pat. Nos. 5,098,468 and 5,035,741 also disclose fatty acid herbicidal compositions that contain C8–12 carbon fatty acids, an oil component, an emulsifier and water. Single phase concentrates are disclosed in U.S. Pat. Nos. 5,098,468 and 5,035,741 that contain the fatty acid(s), oil and emulsifier. The concentrate is diluted with water to form a ready to use composition containing 1–8% by weight fatty acid which is applied at a rate of 8–200 gallons/acre.

Fatty acid herbicides include fatty acid esters of C6–C20 monocarboxylic acids such as those disclosed in U.S. Pat. No. 5,284,819. Additionally, fatty acid salts such as those disclosed in U.S. Pat. Nos. 2,626,862; 4,975,110; and 5,035,741, can be employed as fatty acid herbicides.

Maleic hydrazide (MH) is a plant growth regulator and is registered with the Environmental Protection Agency for certain select uses. On tobacco MH is used to prevent shoots arising from auxiliary buds ("suckers"), thereby maximizing the size and quality of the leaves on the main stem. NH is also commonly applied to potatoes and onions to inhibit sprouting, and to lawns to reduce growth, thereby reducing required maintenance and watering. MH is not regarded as a chemical that kills plants.

Although fatty acid herbicides are considered to be environmentally friendly, they are contact herbicides. Only the treated plant areas become necrotic. Plants with well established root systems are often able to re-grow following treatment with fatty acid herbicides. These weeds include dandelions and thistles. There is a need for products that have the safety of fatty acid herbicides and are able to kill weeds with established root systems.

SUMMARY OF THE INVENTION

The present invention provides an environmentally compatible herbicidal composition which can be advantageously synthesized on an industrial scale. The herbicidal compositions provide effective control of difficult weeds using environmentally friendly compounds.

The present invention is directed to a herbicide which contains, as an effective component, an herbicidally effective mixture of a carboxylic acid component having between one (1) and eighteen (18) carbon atoms and a derivative of maleic hydrazide. Preferably, the pH of the composition is greater than or equal to 6.

The carboxylic acid component of the herbicidal composition includes one or a mixture of alpha monocarboxylic acids having a hydrocarbon chain between one and eighteen carbon atoms. In a preferred embodiment, the hydrocarbon chain is between about two and eleven carbon atoms, most preferably nine or eleven carbon atoms, e.g., nonanoic acid or undecylenic. The hydrocarbon chain can be branched or unbranched, substituted or unsubstituted and/or include one or more sites of unsaturation, e.g., alkyene or alkyne moieties. Preferably, the hydrocarbon chain has nine carbon atoms, and is unbranched, unsubstituted and fully saturated.

The carboxylic acid component in the herbicidal composition is effective as an amide, in the free acid form, or, preferably as a salt. Amides include primary, secondary and tertiary amides. Suitable secondary and tertiary amides can have lower alkyl groups of between one and three carbon atoms. Salts of carboxylic acid include, but are not limited to sodium, potassium, lithium, magnesium, calcium, copper, iron, zinc, manganese, amines, and ammonium. Suitable amines include tertiary amine having lower alkyl groups of between one and three carbon atoms, e.g., triethylamine. Preferred salts include sodium, potassium and ammonium. A preferred salt for the carboxylic acid compositions of the invention is the ammonium salt, i.e., $NH_4^{+1}$.

Derivatives of maleic hydrazide useful in the herbicidal composition include alkylated products of one or both nitrogens within the six membered ring of maleic hydrazide and, preferably, maleic hydrazide salts. Typically the alkylated derivatives of maleic hydrazide are of lower alkyl groups having carbon chain lengths of from one to about four carbon atoms. Salts of maleic hydrazide include, but are not limited to, sodium, potassium, lithium, magnesium, amines and, preferably ammonium salts. Suitable amines include tertiary amine having lower alkyl groups of between one and three carbon atoms, e.g., triethylamine. The concentration of the maleic hydrazide derivative in the herbicidal compositions is between about 0.5 to about 5%, preferably between about 0.5 to 2%, and most preferably about 1%.

The herbicidal compositions of the present invention are herbicides which have little or no residual soil activity as the composition is degraded and used as a nutrient source by soil microorganisms. The compositions are substantially non-toxic to humans and animals.

The herbicidal compositions of the invention are prepared in the form of a concentrate which includes the active ingredients (carboxylic acid component and a derivative of maleic hydrazide, e.g. a salt). As such, the composition can be prepared as a concentrate, which is easily shipped and stored, and can be subsequently diluted with water before use. The concentrate can comprise from approximately 20% to about 80% active ingredients. More preferably, the active ingredient present in the concentrate ranges from between about 20% and about 60%. To prepare a ready to use formulation, the concentrate is diluted with water so as to contain approximately 1% to about 8% active ingredients.

The invention is also drawn to methods for treating undesired grasses or weeds by applying a composition of a herbicidally effective amount of a carboxylic acid component and maleic hydrazide or a derivative of maleic hydrazide to said grasses or weeds, such that said grasses or weeds are controlled. It has been unexpectedly found that maleic hydrazide with a carboxylic acid component, as defined herein, is extremely effective in combating undesired weeds.

Other advantages of the invention will be readily apparent to one having ordinary skill in the art upon reading the following description.

All percentages by weight identified herein are based on the total weight of the herbicidal compositions unless otherwise indicated.

DETAILED DESCRIPTION OF THE INVENTION

The features and other details of the invention will now be more particularly described and pointed out in the claims. It will be understood that the particular embodiments of the invention are shown by way of illustration and not as limitations of the invention. The principle features of this invention can be employed in various embodiments without departing from the scope of the invention.

The present invention is based, at least in part, on a discovery that the present invention provides an environmentally compatible herbicidal composition which includes a carboxylic acid component having between one (1) and eighteen (18) carbon atoms and a derivative of maleic hydrazide. The carboxylic acid component of the herbicidal composition includes one or a mixture of alpha monocarboxylic components having a hydrocarbon chain between one and eighteen carbon atoms. In one embodiment, the hydrocarbon chain is between about 2 and about 11 carbon atoms, most preferably nine carbon atoms, e.g., nonanoic acid. The hydrocarbon chain can be branched or unbranched, substituted or unsubstituted and/or include one or more sites of unsaturation, e.g., alkyene or alkyne moieties. In one embodiment, the hydrocarbon chain is between about 2 and about 11 carbon atoms, preferably nine carbon atoms, and is unbranched, unsubstituted and fully saturated. In another embodiment, the hydrocarbon chain is between about 2 and about 11 carbon atoms, preferably eleven carbon atoms (C11:1), unbranched, unsubstituted and has one degree of unsaturation. Suitable examples include nonanoic, undecylenic, and decanoic acid. Effective concentrations of the carboxylic acid component in the herbicidal composition is between about 1 and about 10%, preferably between about 2 and about 5%, and most preferred about 3.5%.

The carboxylic acid component in the herbicidal composition is effective as an amide, in the free acid form, or, preferably as a salt. The term "carboxylic acid component" is understood to include amides, free acids, and, preferably, salts of carboxylic acids as herein described. Amides of carboxylic acids defined herein include primary, secondary and tertiary amides. Suitable secondary and tertiary amides can have lower alkyl groups of between one and four carbon atoms. Salts of carboxylic acid include, but are not limited to sodium, potassium, lithium, magnesium, calcium, copper, iron, zinc, manganese, amines, and ammonium. Suitable amines include tertiary amines substituted with lower alkyl groups, e.g., triethylamine. Preferred salts include sodium, potassium and ammonium. A preferred salt for the carboxylic acid compositions of the invention is the ammonium salt, i.e., $NH_4^{+1}$.

In one embodiment, the carboxylic acid derivative can be a mixture of free acid or acids, amides, or salts as described herein. The mixture can be of one or more carboxylic acid derivatives, that is, the fatty acid portion can be a mixture of fatty acids as free acids, amides or salts. In certain aspects of the invention, the carboxylic acid is fully saponified, in other aspects the carboxylic acid is partially saponified. Saponification of the carboxylic acid can be as low as 25%, more preferably about 50%, most preferably greater than 75% and in a most preferred embodiment, greater than 90%.

The composition of the invention preferably has a pH greater than or equal to 6. Most preferably, the pH is in the range of about 6 to about 9, e.g., 6.5, 7.0, 7.5, 8.0 and 8.5.

The term "hydrocarbon chain" is recognized by those skilled in the art and includes moieties which are carbon atom based, such as alkyl groups, alkylene groups and alkyne groups, terms which are also recognized in the art.

The term "alkyl" refers saturated aliphatic groups, including straight-chain alkyl groups and branched-chain alkyl groups and substituted alkyl groups which are straight chain or branched. In one embodiment, a straight chain or branched chain alkyl has 30 or fewer carbon atoms in its backbone (e.g., C1–C30 for straight chain, C3–C30 for branched chain), and more preferably 20 or fewer.

Moreover, the term alkyl as used throughout the specification and claims is intended to include both "unsubstituted alkyls" and "substituted alkyls," the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxy alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, aralkyl, or an aromatic or heteroaromatic moiety. It will be understood by those skilled in the art that the moieties substituted on the hydrocarbon chain can themselves be substituted, if appropriate. An "aralkyl" moiety is an alkyl substituted with an aryl (e.g., phenylmethyl (benzyl)).

The term "aryl" as used herein includes 5- and 6-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure may also be referred to as "aryl heterocycles," "heteroaryls" or "heteroaromatics." The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, aralkyl, or an aromatic or heteroaromatic moiety. Aryl groups can also be fused or bridged with alicyclic or heterocyclic rings which are not aromatic so as to form a polycycle (e.g., tetralin).

Unless the number of carbons is otherwise specified, "lower alkyl" as used herein means an alkyl group, as defined above, but having from one to ten carbons, more preferably from one to six carbon atoms in its backbone structure. Preferred alkyl groups are lower alkyls having one to three carbon atoms.

The terms "heterocyclyl" or "heterocyclic group" refer to 3- to 10-membered ring structures, more preferably 4- to 7-membered rings, which ring structures include one to four heteroatoms. Heterocyclyl groups include pyrrolidine, oxolane, thiolane, oxazole, piperidine, piperazine, morpholine, lactones, lactams such as azetidinones and pyrrolidinones, lactones, sultams, sultones, and the like. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, aralkyl, or an aromatic or heteroaromatic moiety. A heteroalkyl moiety is an alkyl substituted with a heteroaromatic group.

The term "fatty acid" can be applied to certain of the carboxylic acid moieties useful in the herbicidal compositions of the invention. The term "fatty acid" is recognized by those having ordinary skill in the art and it is intended to include those saturated or unsaturated straight chain and branched carboxylic acids obtained from the hydrolysis of fats. Examples of suitable fatty acids include nonanoic, undecylenic, and decanoic acid. Therefore, fatty acid components are analogous to the carboxylic acid derivatives described throughout this specification.

The invention also includes similar compounds with oleyl groups.

Derivatives of maleic hydrazide useful in the herbicidal composition include alkylated products of one or both nitrogens within the six membered ring of maleic hydrazide and, preferably, maleic hydrazide salts. Typically the alkylated derivatives of maleic hydrazide are of lower alkyl groups having carbon chain lengths of from one to about four carbon atoms. Salts of maleic hydrazide include, but are not limited to, sodium, potassium, lithium, magnesium, amines and, preferably ammonium salts. Alternatively, salts of maleic hydrazide can be aluminum, calcium, manganese, iron, nickel, copper or zinc salts. The concentration of maleic hydrazide in the herbicidal compositions is between about 0.5 to about 5%, preferably between about 0.5 to 2%, and most preferably about 1%.

Maleic hydrazide (1,2-dihydro-3,6-pyridazine-dione; 3,6-dihydroxypyridazine) is used to prevent potatoes and onions from sprouting, control sucker growth in tobacco and frost protection in citrus plants. Maleic hydrazide is generally recognized as a safe compound. Maleic hydrazide has a chemical structure similar to uracil. Uracil is one of the five common nucleic acids; the other acids being adenine, guanine, cytosine and thymine. Adenine, guanine and cytosine are found in both DNA and RNA, while thymine is only found in DNA, and Uracil is only found in RNA. Uracil and maleic hydrazide have six member rings with four carbon atoms and 2 nitrogen atoms. Two of the carbon atoms have an attached, double-bonded oxygen (C=O). Uracil has nitrogen atoms at the 1 and 3 positions about the ring and the C=O at positions 2 and 4. In contrast, maleic hydrazide has nitrogen atoms at the 1 and 2 positions and the C=O carbons at the 3 and 6 positions.

DNA regulates a plant's growth and responses to damage and attack from outside influences. RNA is transcribed from DNA, which is then used as a template for production of proteins. Maleic hydrazide, it is believed, acts as a uracil anti-metabolite and block miotic division in plants (cell division). The combination of a carboxylic acid component and maleic hydrazide derivative damages plant tissues and impairs the plant's ability to repair such damage. The synergistic effect of the carboxylic acid component and derivative of maleic hydrazide has unexpectedly been found to increase plant mortality.

The herbicidal compositions of the invention can further include various additives to increase the efficacy of the herbicide in destroying undesired weeds. Suitable additives include surfactants, emulsifiers, alcohols, gums, antifoaming agents.

Suitable alcohols useful in the herbicidal compositions include those alcohols having between 1 and about 14 carbon atoms. The alcohols can be straight chained or branched and can contain aromatic moieties such as phenyl rings. Exemplary alcohols include, but are not limited to, methanol, ethanol, propanol, isopropyl alcohol, butyl alcohol, sec-butyl alcohol, tertiary butyl alcohol, hexanol, octanol, decanol, dodecanol, benzyl alcohol and tetrahydrolfurfuralcohol. Preferred alcohols include ethanol, isopropyl alcohol and propanol, with isopropyl alcohol being the most preferred. Typical concentrations of the alcohol portion in the herbicidal composition vary between about 0 to about 10%, preferably between about 2 and about 5%, and most preferably about 2%.

Suitable gums useful in the herbicidal compositions of the invention include those known in the art such as the xanthum gums Kelzan S (Merck & Co.) and Rhodopol 23 (Rhone Poulenc), magnesium aluminum silicates such as Van Gel B (R.T. Vanderbilt), and polyacrylic acid polymers. A preferred gum is Kelzan S. Typically, the concentration of the gum in the herbicidal composition is between about 0 to about 1%.

Antifoaming agents useful in the herbicidal compositions of the invention include those known in the art such as silicone-based prodcuts FG-10 Antifoam (Dow Corning Corp., Midland, Mich., USA). Typical concentrations of antifoaming agents useful in the herbicidal compositions is between about 0 to about 1%.

The herbicidal compositions of the present invention are systemic, non-selective herbicides that can be applied to leaves, stems or roots. Fatty acids when applied with out maleic hydrazide are contact herbicides, only affecting the plant tissue directly in contact with the herbicidal spray. Maleic hydrazide when applied without fatty acids is a translocated growth regulator with no herbicidal activity. The invention is the combination of fatty acids, i.e., carboxylic acid components as defined herein, and maleic hydrazide derivatives which results in a translocated systemic herbicide. In soil, the compositions are readily broken down by microorganisms and used as a food source. The compositions of the invention are substantially nontoxic to humans or animals.

The herbicidal compositions of the invention are prepared in the form of a concentrate which includes the active ingredients (carboxylic acid component and a derivative of maleic hydrazide, e.g., ammonium salts of a carboxylic acid and maleic hydrazide). As such, the composition can be prepared as a concentrate, which is easily shipped and stored, and can be subsequently diluted with water before use. The concentrate can comprise from approximately 10% to about 80% active ingredients. More preferably, the active ingredient present in the concentrate ranges from between about 20% and about 60%. To prepare a ready to use formulation, the concentrate is diluted with water so as to contain approximately 1% to about 8% active ingredients.

The treatment according to the invention may be used to control a broad spectrum of weed species in various agricultural, commercial and domestic situations. The compositions are best applied as early and late post-emergent herbicides. The combined use described above offers both contact and limited residual activity.

By the term "pre-emergence application" is meant application to the soil in which the weeds seeds, or to the aerial or exposed portions of the weeds, before the emergence of the crop plants above the surface of the soil. By the term "foliar activity" is meant herbicidal activity obtained by application to the aerial or exposed portions of the weeds which have emerged above the surface of the soil.

The combination of components of the present invention also may be used advantageously for the control of vegetation. The efficacy for growth control depends, among other things, on the amount of the combination applied per acre, the treatment time, and the type of plant to which it is applied. The inhibiting effects may occur in a manner which produces, for example, total destruction of undesired plants, including leaves, flowers, stems and roots. The combination of agents of the invention also can be used wherever it is desired not to fully destroy undesired plants at once, but to maintain the plants in a vegetative, low growth stage. For this, the incorporation of maleic hydrazide as a derivative or as maleic hydrazide shows beneficial effects.

Illustrative of vegetation that can be controlled by these methods, with or without the use of surfactants are: black mustard (*Brassica nigra*), curly dock (*Rumex crispus*), common groundsel (*Senecio vulgaris*), pineapple weed (*Matricaria matricarioides*), swamp smartweed (kelp) (*Polygonum coccineum*), prickly lettuce (*Lactuca scariola*), lance-leaved groundcherry (*Physalis lanceifolia*), annual sowthistle (*Sonchus oleraceus*), london rocket (*Sisybrium irio*), common fiddleneck (*Amsinckia intermedia*), hairy nightshade (*Solanum sarrachoides*), shepherd's purse (*Capsella bursa-pastoris*), sunflower (*Helianthus annuus*), common knotweed (*Polygonum aviculare*), green amaranth (*Amaranthus hybridus*), mare's tail (*Conyza canadensis*), henbit (*Lamium amplexicaule*), cocklebur (*Xanthium strumarium*), cheeseweed (*Malva parviflora*), lambsquarters (*Chenopodium album*), puncture vine (*Tribulus terrestris*), common purslane (*Portulaca oleracea*), prostrate spurge (*Euphorbia supina*), telegraph plant (*Heterotheca grandiflora*), carpetweed (*Mollugo verticillata*), yellow starthistle (*Centaurea solstitialis*), milk thistle (*Silybum marianum*), mayweed (*Anthemis cotula*), burning nettle (*Urtica urens*), fat hen (*Atriplex patula*), chickweed (*Stellaria media*), scarlet pimpernel (*Anagallis arvensis*) redroot pigweed (*Amaranthus retroflexus*), minnerslettuce (*Montia perfoliata*), turkey mullein (*Eremocarpus setigerus*), nettleleaf goosefoot (*Chenopodium murale*), prostrate pigweed (*Amaranthus blitoides*), silverleaf nightshade (*Solanum elaeagnifolium*), hoary cress (*Cardaria draba*), largeseed dodder (*Cuscuta indecora*), California burclover (*Medicago polymorpha*), horse purslane (*Trianthema portulacastrum*), field bindweed (*Convolvulus arvensis*), Russian knapweed (*Centaurea repens*), flax-leaved fleabane (*Conyza bonariensis*), wild radish (*Raphanus sativus*), tumble pigweed (*Amaranthus albus*), stephanomeria (*Stephanomeria exiqua*), wild turnip (*Brassica campestris*), buffalo goard (*Cucurbita foetidissima*), common mullein (*Verbascum thapsus*), dandelion (*Taraxacum officinale*), Spanish thistle (*Xanthium spinosum*), chicory (*Cichorium intybus*), sweet anise (*Foeniculum vulgare*), annual yellow sweetclover (*Melilotus indica*), poison hemlock (*Conium maculatum*), broadleaf filaree (*Erodium botrys*), whitestem filaree (*Erodium moschatum*), redstem filaree (*Erodium cicutarium*), ivyleaf morning-glory (*Ipomea hederacea*), shortpod mustard (*Brassica geniculata*), buckhorn plantain (*Plantago lacenolata*), sticky chickweed (*Cerastium viscosum*), himalaya blackberry (*Rubus procerus*), purslane speedwell (*Veronica peregrina*), Mexican tea (*Chenopodium ambrosioides*), Spanish clover (*Lotus purshianus*), Australian brassbuttons (*Cotula australis*), goldenrod (*Solidago californica*), citron (*Citrullus lanatus*), hedge mustard (*Sisymbrium orientale*), black nightshade (*Solanum nigrum*), Chinese thornapple (*Datura ferox*), bristly ox tongue (*Picris echioides*), bull thistle (*Cirsium vulgare*), spiny sowthistle (*Sonchus asper*), Tasmanian goosefoot (*Chenopodium pumilio*), goosefoot (*Chenopodium botrys*), wright groundcherry (*Physalis acutifolia*), tomatillo groundcherry (*Physalis philadelphica*), petty spurge (*Euphorbia peplus*), bitter apple (*Cucumis myriocarpus*), indian tobacco (*Nicotiana bigelovii*), common morning-glory (*Ipomoea purpurea*), waterplantain (*Alisma triviale*), smartweed (*Polygonum lapathifolium*), mature sowthistle (*Sonchus asper*), yellow nutsedge (*Cyperus esculentus*), purple nutsedge (*Cyperus rotundus*), lupine (*Lupinus formosus*), and grasses of the family Gramineae such as annual rye grass, blue grass, water grass, barnyard grass, bermuda grass, fescue, mat grass, Johnson grass, and the like.

The herbicidal formulations of this invention can be applied by conventional spraying means. The formulation is most effective when applied to thoroughly cover all of the plant foliage. Most succulent annual weeds and grasses 5 inches or less in height, and top kill of perennials, can be controlled with a spray volume of 8% v/v (3.2% active ingredient v/v/). Larger annual weeds, weeds in dense stands, and more difficult to control perennials may require a spray volume in the range of 10–15% v/v spray solution.

The following non-limiting examples serve to fifrther describe the invention.

EXAMPLE 1

An example of a preferred, concentrate formulation is set forth below

| Ingredient | $NH_4C9$ (23%) % by wt. | $NH_4MH$ (6.9%) % by wt. | $NH_4C9 + NH_4MH$ (23% + 6.9%) % by wt. |
|---|---|---|---|
| Distilled Water | 71.0 | 91.0 | 62.0 |
| Ammonium Hydroxide (28 to 30% $NH_3$) | 7.4 | 3.0 | 10.4 |
| Maleic Hydrazide | 0.0 | 6.0 | 6.0 |
| Nonanoic acid (C9) | 21.0 | 0.0 | 21.0 |
| Antifoam (proprietary) | 0.6 | 0.0 | 0.6 |

These concentrates and their dilutions were labeled "$NH_4C9$" and "NH4MH", and "$NH_4C9+NH_4MH$", with active concentrations expressed as percent "$NH_4C9$" and "$NH_4MH$." $NH_4C9$ represents the ammonium salt of nonanoic acid. $NH_4MH$ represents the ammonium salt of maleic hydrazide. MH is maleic hydrazide.

EXAMPLE 2

Field Dandelion Test: Comparison of $NH_4C9+NH_4MH$ Formulations with Killex, Round Up, and Round Up+$NH_4MH$.

This test compared the herbicidal activity of $NH_4C9$, $NH_4MH$, and $NH_4C9+NH_4MH$ on dandelion mortality. This test also investigated the effect of adding isopropyl alcohol (IPA) to $NH_4C9+NH_4MH$. Nine dandelions were grown in 0.5 m² areas of soil in the field. At the time of spraying the dandelions were very large, with leaves longer than 25 cm. Every treatment was sprayed onto 4 areas of soil. Every 0.5 m² plot received 100 ml of solution (0.2 L/m²). All of the areas were re-sprayed 7 days after the first spray. The number of dead plants was assessed 38 days after the first spray.

Round Up (35.6% glyphosate N-(phosphonomethyl) glycine) produced by Monsanto, Killex (9.5% 2,4-D (2,4-dichlorophenoxy) acetic acid, Mecoprop (5% 2-(4-chloro-2-methylphenoxy)) propanoic acid and 0.9% Dicamba (3,6-dichloro-o-anisic acid) by Green Cross were diluted as per label instructions and included as standards.

|  | Dead Plants (#/36) | Dead Plants (%) |
|---|---|---|
| $NH_4C9$ (3.9%) | 0 | 0 |
| $NH_4MH$ (1.15%) | 1 | 3 |
| $NH_4C9 + NH_4MH$ (3.9% + 1.15%) | 32 | 89 |
| $NH_4C9 + NH_4MH$ (3.9% + 0.9%) | 26 | 72 |
| $NH_4C9 + NH_4MH$ + IPA (3.9% + 1.15% + 5%) | 34 | 94 |
| Round Up 2% | 27 | 75 |
| Round Up + $NH_4C9$ 3.9% (2% + 3.9%) | 22 | 61 |
| Killex 0.6% | 29 | 81 |
| Water | 0 | 0 |
| Untreated | 0 | 0 |

EXAMPLE 3

Dandelion Test of $NH_4C9$, $NH_4MH$ and ($NH_4C9+NH_4MH$)

This test examined $NH_4C9$ combined with a range of $NH_4MH$ concentrations. All of the $NH_4C9$ treatments contained 3.9% $NH_4C9$. All of the solutions were sprayed to wetness onto 10 dandelions. The number of dead plants was assessed 36 days after spraying.

This test indicates that ($NH_4C9+NH4MH$) with NH4MH concentrations of 2.3% and higher provide higher plant mortality than similar solutions with 1.15% or lower NH4MH.

|  | Mortality (#/10 plants) |
|---|---|
| $NH_4C9$ (3.9%) | 0 |
| $NH_4MH$ (1.15%) | 0 |
| $NH_4C9 + NH_4MH$ (3.9% + 0.58%) | 0 |
| $NH_4C9 + NH_4MH$ (3.9% + 1.15%) | 0 |
| $NH_4C9 + NH_4MH$ (3.9% + 2.30%) | 4 |
| $NH_4C9 + NH_4MH$ (3.9% + 5.8%) | 8 |
| Water | 0 |
| Untreated | 0 |

EXAMPLE 4

Greenhouse Dandelion Test of $NH_4MH$ and $NH_4C9$ in Combination With a Gum.

This test studied the effect of thickening $NH_4C9+NH_4MH$ solutions on plant mortality. The solutions were thickened by adding 0.5 g of the xanthan gum Rhodopol 23 suspended in 3.0 g propylene glycol to 96.5 g solution. The pH values of the test solutions were adjusted to 7.38.

Thickening increased the damage caused by $NH_4C9+NH_4MH$. This test also demonstrates the synergy of $NH_4C9$ and $NH_4MH$ combinations.

|  | Viscosity (Cps) | Mortality (#/10) |
|---|---|---|
| $NH_4C9$ (2.2%) | 1 | 1 |
| $NH_4MH$ (1.15%) | 1 | 0 |
| $NH_4C9 + NH_4MH$ (2.2% + 0.58%) | 1 | 3 |
| $NH_4C9$ (2.2%) + gums | 428 | 2 |
| $NH_4MH$ (1.15%) + gums | 288 | 2 |
| $NH_4C9 + NH_4MH$ (2.2% + 0.58%) + gums | 211 | 7 |
| Water | 1 | 0 |
| Untreated |  | 0 |

EXAMPLE 5

Dandelion Herbicide: Comparison of TopGun With and Without MH

TopGun is a proprietary emulsified formulation containing 18% C9 (nonanoic) acid present as free acid. TopGun was diluted to 1.8% C9 acid. Each solution was sprayed to run-off onto ten 20 cm diameter dandelions grown in the greenhouse. The number of dead plants was assessed 15 days after spraying.

These results demonstrate the synergy between C9 and the ammonium salt of maleic hydrazide extends to emulsified free fatty acids.

|  | Number of Dead Plants (#/10 Plants) |
|---|---|
| TopGun | 0 |
| $NH_4MH$ (1.15%) | 0 |
| TopGun + $NH_4MH$ | 3 |
| Water | 0 |
| Untreated | 0 |

EXAMPLE 6
Field Dandelion Test of $NH_4C9+NH_4MH$ With Added Alcohol and Gum.

This test compared the herbicidal activity of $NH_4C9$, $NH_4MH$ and ($NH_4C9+NH_4MH$) with added alcohol and gums on dandelion mortality. The gum Kelzan S (Merck & Co., Inc.) at 0.08% was used as a thickener.

This test also investigated the effect of adding $NH_4MH$ to emulsified C9 acid. The emulsified C9 acid solution was made by adding 3.5 g of C9 acid with 1.0 g of Tween 80 and 95.5 g water (no ammonium hydroxide was added). For the C9 acid+$NH_4MH$ solution, 13 g of water was replaced by 13 g of the 6.9% $NH_4MH$ stock solution.

Every solution was sprayed onto 16 field-grown, medium-sized dandelions. All of the dandelions had leaves longer than 10 cm. The dandelions were sprayed at a rate of 0.2 $L/m^2$. All plants were re-sprayed 14 days after the first spray. The number of dead plants was assessed 10 days after the second spray.

|  | Dead Plants | |
| --- | --- | --- |
|  | (#/16) | (%) |
| $NH_4C9$ (3.9%) | 2 | 13 |
| $NH_4MH$ (0.9%) only | 0 | 0 |
| $NH_4C9$ + $NH_4MH$ (3.9% + 0.9%) | 7 | 44 |
| $NH_4C9$ + $NH_4MH$ + IPA (3.9% + 0.9% + 5%) | 9 | 56 |
| $NH_4C9$ + $NH_4MH$ + gum (3.9% + 0.9% + 0.8%) | 11 | 69 |
| $NH_4C9$ + $NH_4MH$ + IPA + gums (3.9% + 0.9% + 5% + 0.8%) | 11 | 69 |
| C9 acid (3.5%) | 3 | 19 |
| TopGun + $NH_4MH$ (3.5% + 0.9%) | 10 | 63 |
| Water | 0 | 0 |
| Mechanically trimmed | 0 | 0 |
| Untreated | 0 | 0 |

EXAMPLE 7
Dandelion Test of $NH_4C9$ and $NH_4C11:1$, With and Without MH

Five-month-old potted dandelions were sprayed with solutions of ammonium fatty acid soaps in combination with $NH_4MH$. The solutions contained 3.9% ammonium fatty acid soaps and 1.15% $NH_4MH$. The plants were sprayed at a rate of 0.5 $L/m^2$. The plants were sprayed twice, with 8 days between sprays. Final observations were taken 8 days after the second spray. Fifteen plants were used per treatment.

$NH_4C9$ and $NH_4C11:1$ are good contact herbicides, however treated plants were able to re-grow. The addition of $NH_4MH$ to $NH_4C9$ and $NH_4C11:1$ greatly increased plant mortality.

|  | Number of Dead Plants of 15 Total |
| --- | --- |
| MH only (1%) | 0 |
| $NH_4C9$ (3.9%) | 1 |
| $NH_4C11:1$ (3.9%) | 2 |
| $NH_4C9$ + $NH_4MH$ (3.9% + 1.15%) | 7 |
| $NH_4C11:1$ + $NH_4MH$ (3.9% + 1.15%) | 10 |
| Water | 0 |
| Untreated | 0 |

Adding MH or $NH_4MH$ to a $NH_4$ C9 Concentrate

Two solutions were prepare to demonstrate that $NH_4MH$ has superior solubility in $NH_4C9$ concentrate that MH. The compositions of the solutions are listed below. Note that slightly more NH4MH was added than MH acid, as $NH_4MH$ has a higher molecular weight. The same number of moles of $NH_4MH$ and MH were used.

| Ingredient | A "$NH_4C9$ + $NH_4MH$" (23% + 6.9%) % by wt. | B "$NH_4C9$ + MH acid" (23% + 6.0%) % by wt. |
| --- | --- | --- |
| Distilled water | 69.4 | 70.3 |
| $NH_4C9$ | 23.1 | 23.1 |
| Ammonium maleic hydrazide | 6.9 | 0.0 |
| Maleic Hydrazide acid | 0.0 | 6.0 |
| Antifoam (proprietary) | 0.6 | 0.6 |
| pH | 8.4 | 6.8 |
| Viscosity (centipoise $(mPa \cdot s))^1$ | 70 | greater than 4000 |

[1]Viscosity is measured in centipoise (milli pascal seconds). Water has a viscosity of 1.0.

Viscosity is measured in centipoise (milli pascal seconds). Water has a viscosity of 1.0.

Solution "A" was a slightly opaque, uniform and stable in storage. Solution "B" was very thick and gelatinous, resembling partially set gelatin (Jello). After one week at room temperature, Solution "B" contained many clusters of crystals. Solution "A" is well suited for commercial manufacture and use, whereas Solution "B" is not.

Adding MH or $NH_4MH$ to a $NH_4$ C9 Ready-To-Use Solution

Similar to the concentrate solutions, Ready-To-Use solutions were made of $NH_4$ MH or MH acid. The compositions of the solutions were as follows:

| Ingredient | C "$NH_4C9$ + $NH_4MH$" (3.9% + 1.2%) % by wt. | D "$NH_4C9$ + MH acid" (3.9% + 1.0%) % by wt. |
| --- | --- | --- |
| Distilled water | 94.8 | 95.0 |
| $NH_4C9$ | 3.9 | 3.9 |
| Ammonium maleic hydrazide | 1.2 | 0.0 |
| Maleic Hydrazide acid | 0.0 | 1.0 |
| Antifoam (proprietary) | 0.1 | 0.1 |
| pH | 7.7 | 6.8 |

Solution "C" was slightly opaque, uniform and stable in storage. Solution "D" had many gelatinous particles that separated and tended to float to the surface. These products are often sold in containers with a hand-pump sprayer attached to a straw than draws solution from the bottom of the container. If solution "D" were in such a container the composition coming out of the pump could vary depending upon how full the container was. It is very apparent that Solution "C" is well suited for commercial manufacture and use, whereas Solution "D" is not.

Adding MH or $NH_4MH$ to a TopGun Ready-TO-Use Solution

The fatty acid herbicide TopGun is a commonly sold product. It is a proprietary composition of 18% fatty acids and emulsifiers. Adding MH or salts thereof to TopGun greatly enhances its activity (Example 5). TopGun was diluted as per label instructions, replacing some of the water with MH acid and $NH_4MH$. MH acid and $NH_4MH$ were added to Ready-To-Use solutions of TopGun. The compositions of the solutions were as follows:

| Ingredient | E "TopGun + NH₄MH" (2.6% + 1.2%) % by wt. | F "TopGun + MH acid" (2.6% + 1.0%) % by wt. |
|---|---|---|
| Distilled water | 84.3 | 84.5 |
| TopGun (18% fatty acid) | 14.5 | 14.5 |
| Ammonium maleic hydrazide | 1.2 | 0.0 |
| Maleic hydrazide acid | 0.0 | 1.0 |

Dilutions of TopGun were white, opaque solutions. Solution "E" had no crystals visible or sediment, indicating that the NH₄MH was in solution. In contrast, Solution "F" had a layer of sedimented MH acid crystals, indicating most of the MH was not in solution. As much of the MH of Solution "F" was not in solution, it is likely that Solution "F" would be less active than Solution "E". Also, if Solution "F" were in a container with a hand pump, the solution being sprayed could vary depending upon how full the container was. Also the crystals could clog the pump and spray nozzle. It is very apparent that Solution "E" is well suited for commercial manufacture and use, whereas Solution "F" is not.

These three examples clearly show that the use of MH in herbicidal formulations is unstable and unsuitable. However, if NH₄MH is used instead of MH acid, the resulting compositions are suitable.

Those skilled in the art will know, or be able to ascertain, using no more than routine experimentation, many equivalents to the specific embodiments of the invention described herein. These and all other equivalents are intended to be encompassed by the following claims. All publications and references cited herein including those in the background section are expressly incorporated herein by reference in their entirety.

What is claimed is:

1. A herbicidal composition, comprising:
    a contact-acting carboxylic acid component having a hydrocarbon chain of 1 to 18 carbon atoms; and
    a systemic-acting component selected from the group consisting of maleic hydrazide, maleic hydrazide salts, and mixtures thereof.

2. The herbicidal composition of claim 1, wherein the maleic hydrazide salt is an ammonium salt.

3. The herbicidal composition of claim 1, wherein the carboxylic acid component is a linear or branched, saturated or unsaturated carboxylic acid ammonium salt having from 1 to about 18 carbon atoms.

4. The herbicidal composition of claim 1, wherein the carboxylic acid component is an undecylenic acid ammonium salt.

5. The herbicidal composition of claim 1, wherein the carboxylic acid component is a nonanoic acid ammonium salt.

6. The herbicidal composition of claim 1, wherein the carboxylic acid component is a decanoic acid ammonium salt.

7. The herbicidal composition of claim 1, wherein the derivative of maleic hydrazide is an amide.

8. The herbicidal composition of claim 1, wherein the maleic hydrazide salt is a lithium, sodium, magnesium, aluminum, potassium, calcium, manganese, iron, copper, zinc, ammonium, amine, or amide salt.

9. The herbicidal composition of claim 1, wherein the carboxylic acid component is a lithium, sodium, magnesium, aluminum, potassium, calcium, manganese, iron, copper, zinc, ammonium, amine, or amide salt.

10. A method for treating undesired grasses or weeds, comprising the steps of:
    providing a contact-acting carboxylic acid component, and a systemic-acting component selected from the group consisting of maleic hydrazide, maleic hydrazide salts, and mixtures thereof; and
    applying a herbicidally effective amount of the composition to the grasses or weed, such that the grasses or weeds are controlled.

11. The method according to claim 10, wherein the carboxylic acid component is a linear or branched, saturated or unsaturated fatty acid ammonium salt having from 2 to about 18 carbon atoms.

12. The method according to claim 10, wherein the carboxylic acid component is an undecylenic acid ammonium salt.

13. The method according to claim 10, wherein the carboxylic acid component is a nonanoic acid ammonium salt.

14. The method according to claim 10, wherein the carboxylic acid component is a decanoic acid ammonium salt.

15. The method according to claim 10, wherein the derivative of maleic hydrazide is an amide.

16. The method according to claim 10, wherein the carboxylic acid component is a lithium, sodium, magnesium, aluminum, potassium, calcium, manganese, iron, copper, zinc, ammonium, amine, or amide salt.

17. The method according to claim 10, wherein the maleic hydrazide salt is a lithium, sodium, magnesium, aluminum, potassium, calcium, manganese, iron, copper, zinc, ammonium, amine, or amide salt.

* * * * *